United States Patent [19]

Vandenbossche et al.

[11] 4,266,942
[45] May 12, 1981

[54] METHOD FOR THE AUTOMATIC ELECTRO-CHEMICAL DETERMINATION OF THE END POINT OF A TITRATION

[75] Inventors: Chris Vandenbossche, Zwijnaarde; Jacky Vanhumbeeck, Brugge, both of Belgium

[73] Assignee: Siemens Aktiengesellschaft, Berlin & Munich, Fed. Rep. of Germany

[21] Appl. No.: 113,537

[22] Filed: Jan. 21, 1980

[30] Foreign Application Priority Data

Feb. 12, 1979 [DE] Fed. Rep. of Germany ....... 2905287

[51] Int. Cl.$^3$ ...................... G01N 31/16; G01N 27/44
[52] U.S. Cl. .................. 23/230 R; 204/1 T; 364/497; 422/76; 422/77
[58] Field of Search ............................ 422/75, 76, 77; 23/230 R, 230 A; 204/1 T, 195 T; 364/497, 499

[56] References Cited

U.S. PATENT DOCUMENTS

| 3,157,471 | 11/1964 | Harrison | 422/76 |
|---|---|---|---|
| 3,195,982 | 7/1965 | Nicholson | 422/75 X |
| 3,246,952 | 4/1966 | Dawe | 422/77 |
| 3,769,178 | 10/1973 | Rothermel, Jr. | 422/76 X |
| 4,058,365 | 11/1977 | Krogh | 23/230 R |
| 4,180,440 | 12/1979 | Gibboney et al. | 422/75 |

OTHER PUBLICATIONS

Ebel, "Evaluation of Automated Potentiometric Titrations", *Chemie-Ingenieur-Technik*, vol. 46, 1974, No. 19, pp. 811-817.

*Primary Examiner*—Ronald Serwin
*Attorney, Agent, or Firm*—Hill, Van Santen, Steadman, Chiara & Simpson

[57] ABSTRACT

A method for the automatic, electro-chemical determination of the end point of titration utilizing an initial, continuous addition of the titrant, up to a predetermined value, followed by a step-by-step addition with a resting time inserted therebetween for stabilization of the solution is disclosed. As the titrant is being added to the bath sample in constant volume units, a measured value is formed after every such addition. The difference to the preceding measurement is determined and the three consecutive differences of greatest magnitude are utilized in a mathematical formula for calculating the end point. The titration ceases when the greatest difference lies between two lesser values.

7 Claims, 2 Drawing Figures

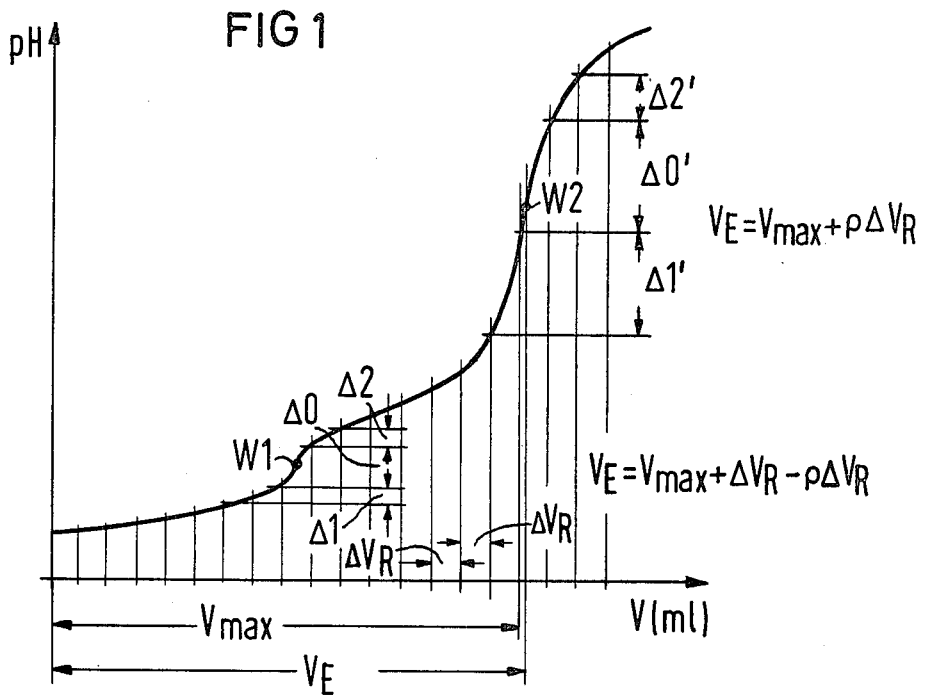
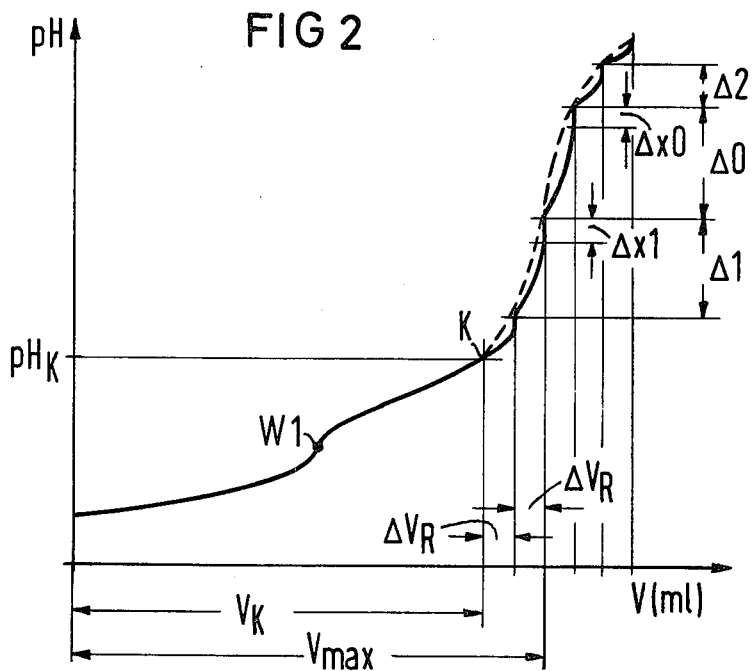

METHOD FOR THE AUTOMATIC ELECTRO-CHEMICAL DETERMINATION OF THE END POINT OF A TITRATION

BACKGROUND OF THE INVENTION

1. Field of the Invention

The present invention relates to a method for the automatic electro-chemical determination of the end point of a titration, and more particularly to such a method in which the titration agent or titrant is added to a sample in constant volume units, a value is formed by measurement after each titrant addition, the magnitude of the difference from the preceding value or step is calculated after each value formation, and, to calculate the end point $V_E$, the three steps of greatest magnitude immediately following one another are used, with the titration ceasing when the highest step value lies between two lesser step values.

2. Description of the Prior Art

Methods of this type are described in greater detail in the periodical "Chemie-Ing.-Technik", Vol. 46, 1974, No. 19, Pages 811–817. This reference concerns the automation of potentiometric titrations. It is stated therein that sufficient significant problems result upon the evaluation of such automated titrations, that an automatic titration to an end value when given in terms of electrical potential is only possible in a few cases. The article therefore proposes to employ known methods of approximation to calculate the titration end point. These methods of approximation allow the use of simple, programmable computers. In addition, the known methods of approximation proceeds from the assumption that the end point and the turning point of the titration curve coincide. However, since the titration curve is generally not symmetrical at this point, one obtains as quotients, the three largest potential steps, (given the precondition of equi-distant titration agent additions). Appropriate equations for the approximate calculation of the end point of automated potentiometric titrations are given in Table 1 on page 813 of the said article. The inventive method, as later described, also makes use of such a known method of approximation.

As indicated in this article, the disadvantage of all of these known methods of approximation is that only three measuring points in the proximity of the end point are employed for the evaluation. It is precisely these measuring points that are typically most affected with errors caused by: the kinetics of the potential adjustment of the electrode, or the kinetics of the equilibrium adjustment regarding the chemical reaction of the titration.

Although these errors can be kept small within certain limits by the very slow addition of the titrant, this, however, results in very long titration times.

An additional significant problem which confronts the introduction of automated titrations when accomplished according to these methods of approximation occurs because the titration curve can contain more than one turning point or point of inflection and the automatic control is not able to distinguish which end point is actually the desired one.

This problem is explained in greater detail on the basis of FIG. 1 which shows a typical titration curve of an alkali in a galvanic bath being titrated with an acid, and which exhibits a second inflection point in the lower range. The titration agent additives or titrants are indicated on the abscissa axis in units of milliliters and the corresponding electrical measuring signals are indicated on the ordinate axis. These measuring signals can be proportional to the pH value. The first turning point is referenced by W1 and the second point by W2. As can be seen from the drawing, a maximum potential step $\Delta 0$ already occurs at the first turning point W1, which is followed by a smaller potential step $\Delta 2$ or, respectively, is preceded by a smaller potential step $\Delta 1$. The first end point occurs due to the reaction of an additional bath component with the titrant, which, however, is of secondary significance for the desired titration. What is desired, however, is obtaining the second end point W2, which is characteristic for the titration of this alkali.

SUMMARY OF THE INVENTION

An object of the present invention is to develop a method of the type as it was initially described, in such a manner that the titration end point cannot only be determined precisely and in a shorter time, but is also suitable for titration curves having a number of inflection points. The inventive method is characterized in that the addition of the titration agent ensues continuously up to a selectively predetermined value using a motorized piston burette. After attainment of this predetermined value, the titration agent is added in constant volume units by means of an appropriate, stepwise control of the burette motor. After each individual titration agent addition, a constant resting time is also inserted for stabilization of the solution before the measuring signal is seized, i.e., selected for use in the additional computations.

Since the titration agent addition ensues continuously at the beginning of the titration until a predetermined value, not only can the time for the titration be considerably reduced, but the undesired titration inflection points can be completely eliminated. The insertion of a resting time before the seizure of the measuring signal, allows a stabilization of the measuring value after every titrant addition. The reproducibility of the measurement is thereby significantly increased.

Upon employment of a pH value measurement for calculating the titration end point, the predetermined value for the continuous titration can be a pH value. A particularly simple value designation is where a specific volume value is prescribed. This then can be accomplished in a simple manner by means of an appropriate determination of the path of the motorized piston burette.

Various other objects, advantages, and features of the present invention will become readily apparent from the ensuing detailed description and the novel features will be particularly pointed out in the appended claims.

BRIEF DESCRIPTION OF THE DRAWINGS

FIG. 1 is a graph of the relationship between the volume of titrant added to the analyte and the pH value of the solution thereby obtained.

FIG. 2 is a graph similar to FIG. 1 and in addition showing the lag time of the measured value for the pH of the solution.

DESCRIPTION OF THE PREFERRED EMBODIMENTS

The inventive method is explained in greater detail with the assistance of FIG. 2. In order to eliminate the first stage with the turning point W1, the control is given a $pH_K$ value which is certain to prevent the control from interference by the turning point W1. In the same manner, a volume value $V_K$ can also be given to the control. Up to this value K, the titration agent is added at a relatively high speed, whereby the burette motor turns continuously. After point K, an appropriate plurality of control pulses are supplied to the motor. These control pulses correspond to the volume units $\Delta V_R$. As is apparent from FIG. 2, the titration curve after the value K has a somewhat angular course which occurs because after the end of the titration agent addition, the output signal still increases by an amount $\Delta x$. By inserting a resting time at the end of each titration agent addition, a stabilization of the measurement occurs. By so doing, the precision and reproducibility is significantly increased.

Accordingly, the titration end point $V_E$ is calculated as follows:

$V_E = V_{max} + \Delta V_R - \rho \Delta V_R$ when $\Delta 1$ lies after $\Delta 0$ and $V_E = V_{max} + \rho \Delta V_R$, when $\Delta 1$ lies before $\Delta 0$, whereby $\rho$, $R_1$ and $R_2$ are auxiliary magnitudes which are determined as follows:

$\rho = 0.5 \, R_2 - 0.2 \, R_1^2$;

$R_1 = \Delta 1/\Delta 0$; and $R_2 = \Delta 2/\Delta 1$, whereby $V_{max}$ signifies the total volume of the titration agent before the largest potential step $\Delta 0$ and $\Delta 0$, $\Delta 1$ and $\Delta 2$ signify the potential steps arranged according to decreasing size.

For example, given the potentiometric titration of a sodium hydroxide solution in a chemical copper bath using a diluted hydrochloric acid as the titrant, the predetermined pH value is selected equal to 9. Expediently, a volume of 0.2 ml is selected for the titrant addition and a constant resting time or, respectively, a resting time proportional to the size of the potential step of 5 through 30 seconds is selected.

The titration continues using the plurality of control pulses to add the volume units $\Delta V_R$ to the analyte. A measurement of the pH is then taken, (after a delay corresponding to the resting time), and the difference between it and the previous step is calculated. For calculating the end point $V_E$, the three additions generating pH values having the largest differences are utilized. The titration is interrupted when the highest value lies between the two other values.

While we have disclosed an exemplary method to illustrate the principles of the invention, it should be understood that we wish to embody within the scope of the patent warranted hereon all such modifications as reasonably and properly come within the scope of our contribution to the art.

We claim as our invention:

1. An improved method for the automatic, electrochemical determination of the end point of a titration of the type in which the titrant is added to a bath sample in constant volume units, a measured value is formed after every titrant addition, the difference from the preceding value is formed after every measured value formation, and the three consecutive additions having the greatest caculated differences are utilized in calculating the end point and wherein the titration is interrupted when the greatest difference lies between two lesser differences, the improvement comprising:

continuously adding the titrant to the initial bath sample, up to a selectively predetermined value thereafter adding the titrant in constant volume units in a step-wise manner; and separating each of said constant volume additions by a resting period of time in order to allow the solution to stabilize prior to obtaining the measured value.

2. An improved method for the automatic, electrochemical determination of the end point of a titration as described in claim 1, wherein said resting period is constant.

3. An improved method for the automatic, electrochemical determination of the end point of a titration as described in claim 1, wherein said resting period is proportional to the previous calculated difference.

4. An improved method for the automatic, electrochemical determination of the end point of a titration as described in claim 1, in which said measured value is a pH value wherein the selectively predetermined value is a pH value.

5. An improved method for the automatic, electrochemical determination of the end point of a titration as described in claim 1, wherein said selectively predetermined value is a volume value.

6. An improved method for the automatic, electrochemical determination of the end point of a titration as described in claim 1, wherein the measured values are potentiometrically attained.

7. An improved method for the automatic, electrochemical determination of the end point of a titration as described in claim 1, in which the end point is automatically calculated according to the following formulas:

$V_E = V_{max} + \Delta V_R - \rho \Delta V_R$, when $\Delta 1$ is after $\Delta 0$; and $V_E = V_{max} + \Sigma \Delta V_R$, when $\Delta 1$ is before $\Delta 0$, wherein $\rho$, R, and $R_2$ are auxiliary magnitudes which are determined as follows:

$\rho = 0.5 \, R_2 - 0.2 \, R_2$;

$R_1 = \Delta 1/\Delta 0$; and $R_2 = \Delta 2/\Delta 1$, and wherein $V_{max}$ signifies the total volume before the largest difference $\Delta 0$, and $\Delta 0$, $\Delta 1$, and $\Delta 2$ signify the calculated differences arranged according to decreasing size.

* * * * *